United States Patent
Mashita

(10) Patent No.: US 12,392,697 B2
(45) Date of Patent: Aug. 19, 2025

(54) EVALUATING PERFORMANCE METHOD AND SYSTEM FOR ELASTIC MATERIAL

(71) Applicant: Sumitomo Rubber Industries, Ltd., Kobe (JP)

(72) Inventor: Ryo Mashita, Kobe (JP)

(73) Assignee: SUMITOMO RUBBER INDUSTRIES, LTD., Kobe (JP)

( * ) Notice: Subject to any disclaimer, the term of this patent is extended or adjusted under 35 U.S.C. 154(b) by 508 days.

(21) Appl. No.: 17/665,741

(22) Filed: Feb. 7, 2022

(65) Prior Publication Data

US 2022/0283066 A1 Sep. 8, 2022

(30) Foreign Application Priority Data

Mar. 4, 2021 (JP) .................................. 2021-034670

(51) Int. Cl.
*G06K 9/00* (2022.01)
*G01N 3/08* (2006.01)
(Continued)

(52) U.S. Cl.
CPC ................. *G01N 3/08* (2013.01); *G01N 3/56* (2013.01); *G01N 9/24* (2013.01); *G01N 23/046* (2013.01);
(Continued)

(58) Field of Classification Search
CPC ... G06T 7/0002; G06T 7/0004; G06T 7/0006; G06T 2207/30108; G06T 2207/30112;
(Continued)

(56) References Cited

U.S. PATENT DOCUMENTS

| 6,874,370 B1 * | 4/2005 | Vachon | G01N 3/32 73/808 |
| 11,002,649 B1 * | 5/2021 | Boyce | G01N 3/04 |

(Continued)

FOREIGN PATENT DOCUMENTS

| JP | 2017-83182 A | 5/2017 |
| JP | 2020-8282 A | 1/2020 |
| JP | 2020-8329 A | 1/2020 |

OTHER PUBLICATIONS

Extended European Search Report for European Application No. 22158561.5, dated Aug. 19, 2022.

*Primary Examiner* — Atiba O Fitzpatrick
(74) *Attorney, Agent, or Firm* — Birch, Stewart, Kolasch & Birch, LLP

(57) ABSTRACT

A performance evaluation method for elastic material including rubber or elastomer, the method includes a strain applying step of applying a strain to a test piece made of an elastic material, an imaging step of obtaining projected images of the test piece being strained by irradiating X-rays to the test piece, a detection step of detecting low-density regions in the test piece based on the projected images, wherein each low-density region is a region where density of a part of the elastic material becomes lower than that before receiving the strain, a relationship obtaining step of obtaining a density distribution between the densities and frequency of the low-density regions based on the detected low-density regions, and a distribution width calculation step of calculating a distribution width specified by a full width at half maximum FWHM from the density distribution approximated to a normal distribution.

11 Claims, 7 Drawing Sheets

(51) Int. Cl.
*G01N 3/56* (2006.01)
*G01N 9/24* (2006.01)
*G01N 23/046* (2018.01)
*G01N 23/083* (2018.01)
*G01N 33/44* (2006.01)
*G06T 7/00* (2017.01)

(52) U.S. Cl.
CPC ......... *G01N 23/083* (2013.01); *G01N 33/445* (2013.01); *G06T 7/0004* (2013.01); *G01N 2203/0017* (2013.01); *G01N 2203/0252* (2013.01); *G01N 2203/0266* (2013.01); *G01N 2203/0647* (2013.01); *G01N 2223/1016* (2013.01); *G01N 2223/401* (2013.01); *G01N 2223/419* (2013.01); *G01N 2223/505* (2013.01); *G01N 2223/601* (2013.01)

(58) Field of Classification Search
CPC .... G06T 7/40; G06T 7/41; G06T 7/44; G06T 2207/10116; G06T 2207/10072; G06T 2207/10081; G01N 2223/401; G01N 23/185; G01N 23/18; G01N 2203/0058; G01N 2203/006; G01N 2203/0069; G01N 2203/0073; G01N 2203/0075; G01N 2203/0091; G01N 2203/0092; G01N 2203/0094; G01N 3/56; G01N 2203/00; G01N 2203/0001; G01N 2203/0014; G01N 2203/0016; G01N 2203/0017; G01N 3/08; G01N 2223/607; G01N 2203/0641; G01N 2203/0647; G01N 2223/1016; G01N 2223/101; G01N 23/083; G01N 23/085; G01N 23/087; G01N 2223/419; G01N 23/046; G01N 33/445; G01N 33/44; G01N 2223/627

See application file for complete search history.

(56) References Cited

U.S. PATENT DOCUMENTS

| | | | |
|---|---|---|---|
| 2014/0037217 A1* | 2/2014 | Iliopoulos | G06T 7/285 382/201 |
| 2014/0044315 A1* | 2/2014 | Derzhi | G06T 15/08 382/109 |
| 2014/0098936 A1* | 4/2014 | Grossnickle | G01N 23/087 428/209 |
| 2016/0275688 A1* | 9/2016 | Chiang | G06T 7/514 |
| 2016/0370269 A1* | 12/2016 | Hsueh | G01N 3/08 |
| 2017/0018096 A1* | 1/2017 | Sungkorn | G01N 33/24 |

* cited by examiner

EVALUATING PERFORMANCE METHOD AND SYSTEM FOR ELASTIC MATERIAL

RELATED APPLICATIONS

This application claims the benefit of foreign priority to Japanese Patent Application No. JP2021-034670, filed Mar. 4, 2021, which is incorporated by reference in its entirety.

FIELD OF THE INVENTION

The present disclosure relates to performance evaluation method and system for elastic material.

BACKGROUND OF THE INVENTION

The Patent document 1 discloses a method for evaluating performance of an elastic material. The method includes a step of applying strain to a test piece made of an elastic material, an imaging step of obtaining the projected images by irradiating X-rays to the test piece, and an evaluation step of evaluating the performance of the elastic material based on the density distribution of the elastic material measured from the projected images.

PATENT DOCUMENT

[Patent document 1] Japanese Unexamined Patent Application Publication 2017-83182

SUMMARY OF THE INVENTION

While the above method is effective as a new evaluation technique to replace the Ramborn wear tester, there is room for further improvement in improving the evaluation accuracy.

The present disclosure has been made in view of the above circumstances, and has a major object to provide performance evaluation method and system for elastic material capable of evaluating performance of the elastic material with high accuracy.

In one aspect of the present disclosure, a performance evaluation method for elastic material including rubber or elastomer, the method includes a strain applying step of applying a strain to a test piece made of an elastic material, an imaging step of obtaining projected images of the test piece being strained by irradiating X-rays to the test piece, a detection step of detecting low-density regions in the test piece based on the projected images, wherein each low-density region is a region where density of a part of the elastic material becomes lower than that before receiving the strain, a relationship obtaining step of obtaining a density distribution between the densities and frequency of the low-density regions based on the detected low-density regions, and a distribution width calculation step of calculating a distribution width specified by a full width at half maximum FWHM from the density distribution approximated to a normal distribution.

DETAILED DESCRIPTION OF THE INVENTION

Figure 1:
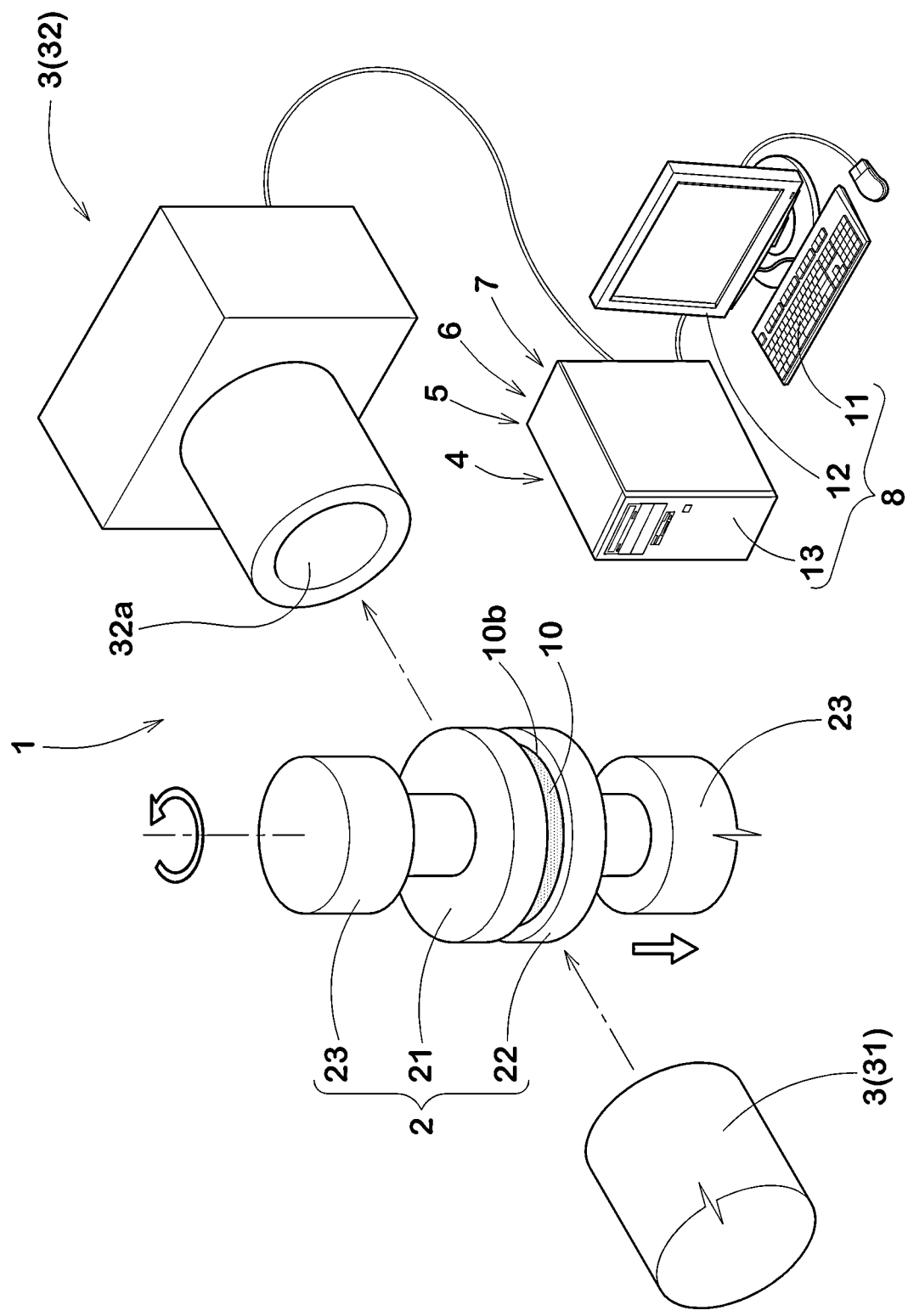
FIG. 1 is a perspective view of a performance evaluating system for elastic material in accordance with the present embodiment.

Hereinafter, one or more embodiments of the present disclosure will be described with reference to the drawings. It should be noted that the drawings contain exaggerated expressions and expressions that differ from the dimensional ratio of the actual structure in order to help the understanding of the content of the disclosure. Further, throughout the embodiments, the same or common elements are given the same reference numerals, and duplicate explanations are omitted. Furthermore, note that the specific configurations shown in the embodiments and drawings are for understanding the contents of the present disclosure, and the present disclosure is not limited to the specific configurations shown in the drawings.

In the performance evaluation method for elastic material in accordance with the present embodiment (hereinafter, may be simply referred to as "performance evaluation method"), performance of an elastic material including rubber or elastomer can be evaluated. The elastic material can be selected as appropriate. As an example of the elastic material of the present embodiment includes rubber obtained using one or more kinds of conjugated diene compounds. Further, as rubber (an elastic material), for example, a rubber for tires can be selected. As an example of the performance evaluated by the method of the present embodiment, wear resistance performance can be selected.

[Performance Evaluation System for Elastic Material]

As the performance evaluation method of the present embodiment, a performance evaluation system for elastic material (hereinafter, may be simply referred to as "performance evaluation system") 1 can be used. FIG. 1 illustrates a perspective view of the performance evaluation system 1 in accordance with the present embodiment.

The performance evaluation system 1 is for evaluating performance of elastic material. The performance evaluation system 1 according to the present embodiment includes a strain applying device 2, an imaging unit 3, a detection unit 4, a relationship obtaining unit 5, and a distribution width calculation unit 6. Further, the performance evaluation system 1 according to the present embodiment may further include an evaluation unit 7.

[Strain Applying Device]

The strain applying device 2 according to the present embodiment is for applying a strain to a test piece 10 made of an elastic material. The strain applying device 2 according to the present embodiment includes a pair of jigs 21 and 22 to which the test piece 10 is fixed, and drive units 23 that relatively moves the jigs 21 and 22 to distort the test piece 10.

The drive units 23, under a condition that one of the jigs 21 is fixed, move the other one of the jigs 22 in a direction that the jigs 21 and 22 are separated from one another. The drive units 23 according to the present embodiment move the other one of the jigs 22 in the axial direction of the test piece 10 which has a columnar shape. Thus, the test piece 10 is stretched in the axial direction and receives a strain.

The strain or the load that applies to the test piece 10 is measured using a load cell (not illustrated) and the like. The position and format of the load cell may be arbitrary. Using such a strain applying device 2, a predetermined strain or load can be applied to the test piece 10. The drive units 23 according to the present embodiment can also rotate the test piece 10 as well as the jigs 21 and 22 around the central axis of the test piece 10.

[Imaging Unit]

The imaging unit 3 according to the present embodiment can obtain projected images of the test piece 10 by irradiating X-rays to the test piece 10 being strained. The imaging unit 3 according to the present embodiment includes an X-ray tube 31 that irradiates X-rays and a detector 32 that detects X-rays and converts them into electrical signals. The imaging unit 3 can obtain projection images of the test piece 10 over the entire circumference by taking multiple projected images with the test piece 10 while the test piece is rotated around the central axis.

The detector 32 may include a phosphor 32a for converting X-rays into visible light. The decay time of the phosphor 32a can be set as appropriate. If the decay time of the phosphor 32a exceeds 100 ms, when the projected images are continuously photographed while the test piece 10 is rotated around the central axis, the afterimage of the previously captured projected image may affect the later projected image. From this point of view, the decay time of the phosphor 32a is preferably equal to or less than 100 ms, more preferably equal to or less than 50 ms, still further preferably equal to or less than 10 ms.

[Detection Unit, Relationship Obtaining Unit, Distribution Width Calculating Unit, Evaluation Unit]

Figure 2:
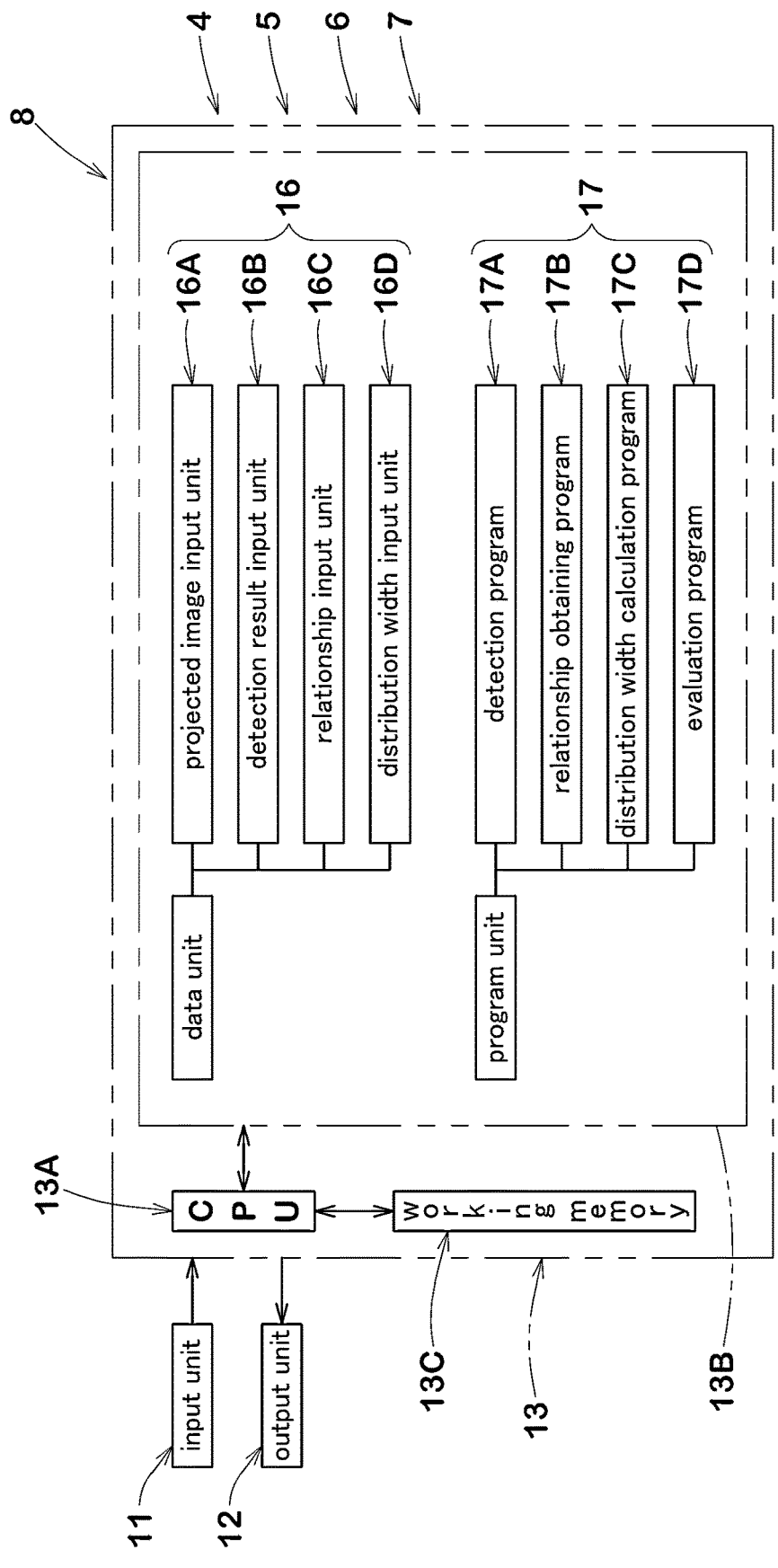
FIG. 2 is a block diagram of a computer in accordance with the present embodiment.

In the present embodiment, the detection unit 4, the relationship obtaining unit 5, the distribution width calculation unit 6 and the evaluation unit 7 are configured as components of a computer 8. FIG. 2 illustrates a block diagram of the computer 8 in accordance with the present embodiment.

The computer 8 according to the present embodiment includes an input unit 11 as an input device, an output unit 12 as an output device, and an arithmetic processing unit 13.

For the input unit 11, a keyboard or mouse may be used, for example. For the output unit 12, a display device or printer may be used, for example. The arithmetic processing unit 13 may be configured to include a central processing unit (CPU) 13A which performs various operations, a storage unit 13B for storing data, programs, etc., and a working memory 13C.

The storage unit 13B, for example, is a device which includes a non-volatile information storage device including magnetic disks, optical disks, SSDs, etc. The storage unit 13B works as a data unit 16 and a program unit 17.

In the present embodiment, the data unit 16 includes a projected image input unit 16A, a detection result input unit 16B, a relationship input unit 16C, and a distribution width input unit 16D. The data input to these will be explained in the processing procedures of the performance evaluation method described later.

In the present embodiment, the program unit 17 is configured as a computer program. The program unit 17 according to the present embodiment includes a detection program 17A, a relationship obtaining program 17B, a distribution width calculation program 17C, and an evaluation program 17D. These programs 17A to 17D can be executed by the central processing unit 13A to make the computer 8 function as the detection unit 4, the relationship obtaining unit 5, the distribution width calculation unit 6, and the evaluation unit 7. These functions are explained in the processing procedures of the performance evaluation method described later.

[Performance Evaluation Method for Elastic Material]

Figure 3:
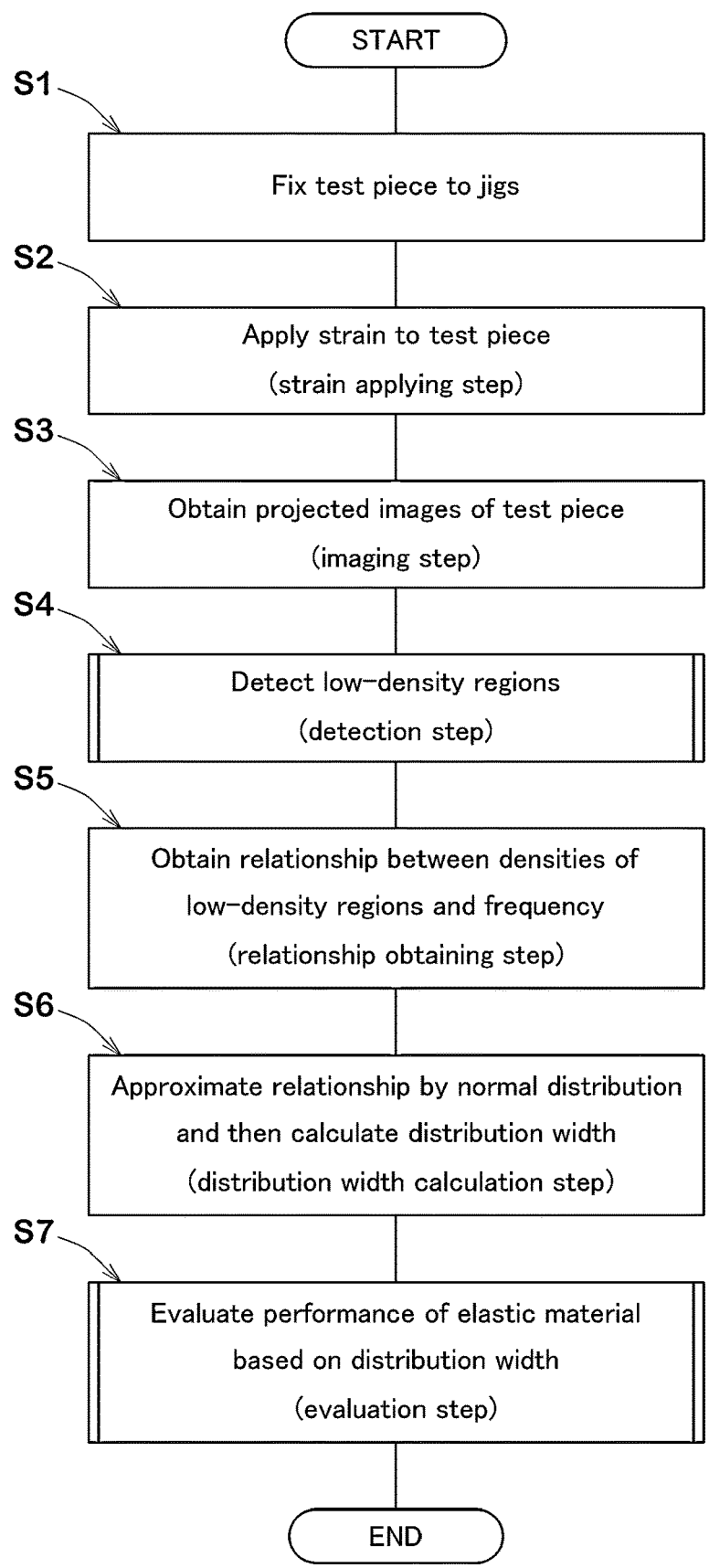
FIG. 3 is a flowchart showing processing procedures of a performance evaluating method for the elastic material in accordance with the present embodiment.

Next, the processing procedures of the performance evaluation method of the present embodiment will be explained. FIG. 3 is a flowchart showing the processing procedures of the performance evaluation method for elastic material of the present embodiment.

[Process of Fixing Test Piece]

In the performance evaluation method of the present embodiment, first, the test piece 10 is fixed to the jigs 21 and 22 as shown in FIG. 1 (step S1). In the present embodiment, the above-mentioned elastic material having a uniform density distribution (e.g., a rubber) is used for the test piece 10. The test piece 10 is formed in a columnar shape same as in Patent Document 1. The details of the test piece 10 and the procedures for fixing the test piece 10 to the jigs 21 and 22 are as described in Patent Document 1, which is incorporated by reference.

[Strain Applying Step]

Next, in the performance evaluation method according to the present embodiment, a strain is applied to the test piece 10 (strain applying step S2). In the strain applying step S2, the jigs 21 and 22 of the strain applying device 2 are relatively moved in the axial direction of the columnar test piece 10 in the direction away from each other using the drive units 23 of the strain applying device 2. Thus, due to the strain applying step S2, the test piece 10 is stretched so that the test piece 10 receive a strain.

In the strain applying step S2 according to the present embodiment, stress is generated inside the test piece 10 due to the strain applied to the test piece 10, and the density of the elastic material is biased. As a result, low-density regions are generated inside the test piece 10.

Figure 4A:
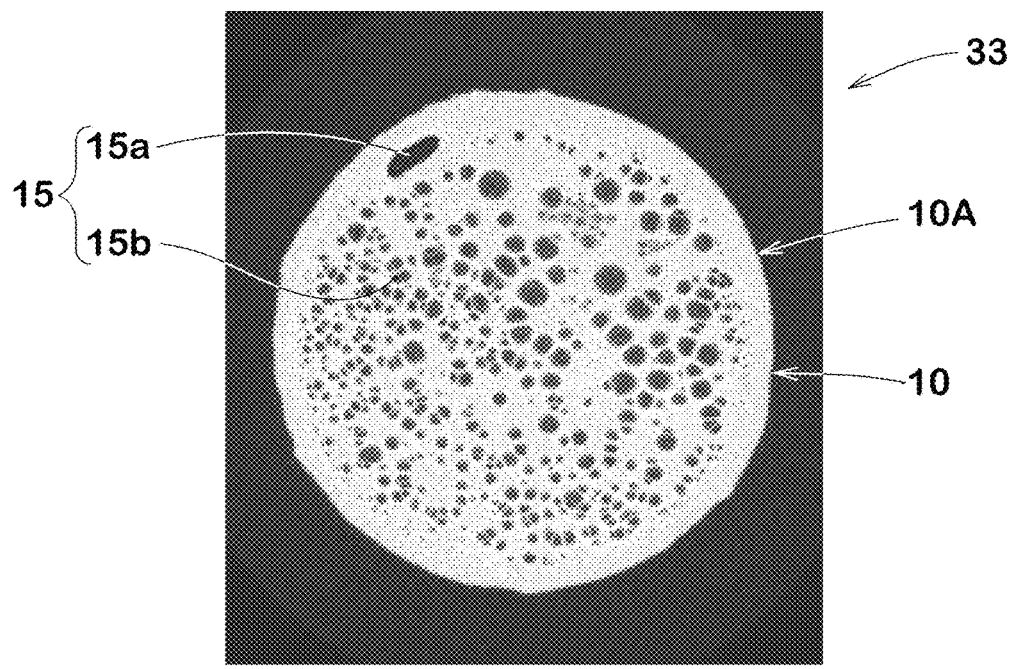
FIGS. 4A and 4B are tomographic images of two test pieces made of elastic materials with different compositions.
Figure 4B:
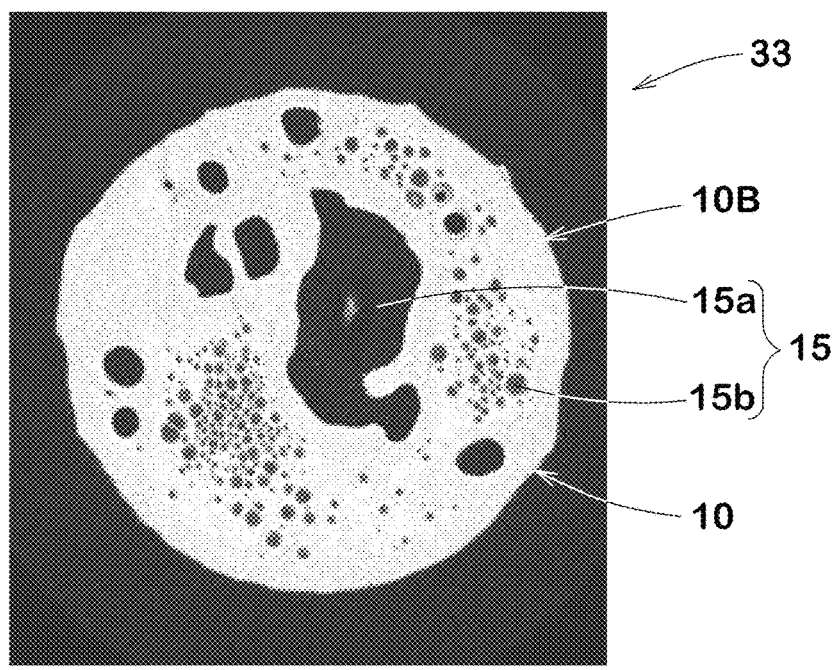

FIGS. 4A and 4B are tomographic images of two test pieces 10A and 10B, respectively, made of elastic materials with different compositions. These tomographic images are obtained in an imaging step S3 described later. These tomographic images show cross sections of the test pieces 10 cut at any plane that intersects perpendicular to the axial direction of each test piece 10 shown in FIG. 1. The low-density regions 15 (void 15a, and low-density rubber portions 15b) are shown in black and light black.

Each low-density region 15 is the region of the test pieces 10 where the density of the elastic material is lower than before it was strained. In the present embodiment, the region having a density in a range of from 0.0 to 0.8 times the density of the elastic material before the strain is applied is defined as the low-density region 15.

In the present embodiment, the low-density regions 15 include one or more voids 15a and one or more low-density rubber portions 15b. The voids 15a according to the present embodiment are defined as regions having a density of from 0.0 to less than 0.1 times (i.e., less than 0.1 times) of the density of the elastic material before the strain is applied. On the other hand, the low-density rubber portions 15b according to the present embodiment are defined as regions having a density of from 0.1 to 0.8 times of the density of the elastic material before the strain is applied.

In the strain applying step S2 according to the present embodiment, tensile strain is applied to the test piece 10, for example. Thus, the low-density regions 15 can be generated efficiently in the elastic material (the test piece 10) as compared to the case where other strains, e.g., compressive strain and shear strain, are applied.

In order to effectively exert the above effects, the tensile strain is preferably equal to or more than 20%. When the tensile strain is equal to or more than 20%, the low-density regions 15 having a sufficient volume are generated in the elastic material, and the evaluation accuracy of the performance of the elastic material may be improved. On the other hand, if the tensile strain becomes larger than necessary, the test piece 10 may be destroyed. Thus, the tensile strain is preferably equal to or less than 100%. In the present embodiment, tensile strain represents a displacement (%) of the test piece 10, which is calculated that a displacement of the strained test piece (the displacement of the test piece 10 from before receiving a strain) is divided by the axial length of the test piece 10 before receiving the strain (a reference length in the extension direction of the test piece 10).

A magnitude of the stress acting on the test piece 10 can be set as appropriate. Here, if the stress is small, the low-density regions 15 (shown in FIGS. 4A and 4B) may not be generated in the test piece 10. From this view point, the stress acting on the test piece 10 is preferably equal to or more than 0.5 MPa. On the other hand, if the stress acting on the test piece becomes greater than necessary, the test piece 10 may be destroyed. From this view point, the stress acting on the test piece 10 is preferably equal to or less than 2.0 MPa.

[Imaging Step]

Next, in the performance evaluation method according to the present embodiment, as shown in FIG. 1, the strained test piece 10 is irradiated with X-rays, and projected images of the test piece 10 are obtained (imaging step S3). The imaging step S3 according to the present embodiment is performed by the computer tomography method.

In the imaging step S3 according to the present embodiment, first, as shown in FIG. 1, the test piece 10 is irradiated with X-rays from the X-ray tube 31. The X-rays pass through the test piece 10 and are detected by the detector 32. The detected X-rays are converted into electrical signals which are output to the computer 8. The computer 8 processes these electrical signals to obtain projected images of the test piece 10.

In the imaging step S3 according to the present embodiment, a plurality of projected images (rotation series images) is obtained by rotating the test piece 10 around the axial direction. Then, in the imaging step S3, multiple projected images (rotation series images) were reconstructed by computer tomography method, and a three-dimensional tomographic image of the test piece 10 (as an example, shown in FIG. 4A) is obtained. The projected images of the test piece 10 are input to the projected image input unit 16A (shown in FIG. 2) of the computer 8.

The brightness of X-rays can be set as appropriate. The brightness of X-rays may be greatly related to the S/N ratio of the X-ray scattering data. When the brightness of the X-rays becomes low, the signal intensity tends to be weaker than the X-ray statistical error, and it may be difficult to obtain data with a sufficiently high S/N ratio even if the measurement time is lengthened. From this point of view, the brightness of the X-rays (photons/s/mrad$^2$/mm$^2$/0.1% bw) is preferably equal to or more than $10^{10}$, more preferably equal to or more than $10^{12}$.

The decay time of the phosphor 52a for converting X-rays to visible light can be set as appropriate. Similar to Patent Document 1, the decay time of the phosphor 32a is preferably equal to or less than 100 ms, more preferably equal to or less than 50 ms, still further preferably equal to or less than 10 ms, in view of preventing the afterimage of the previously captured projected image from affecting the later captured projected image.

[Detection Step]

Next, in the performance evaluation method according to the present embodiment, the low-density regions 15 (shown in FIG. 4A) are detected in the test piece 10 based on the projected images (detection step S4). Here, the low-density regions 15 are regions where densities of some portions of the elastic material are lower than that before being strained.

Figure 5:
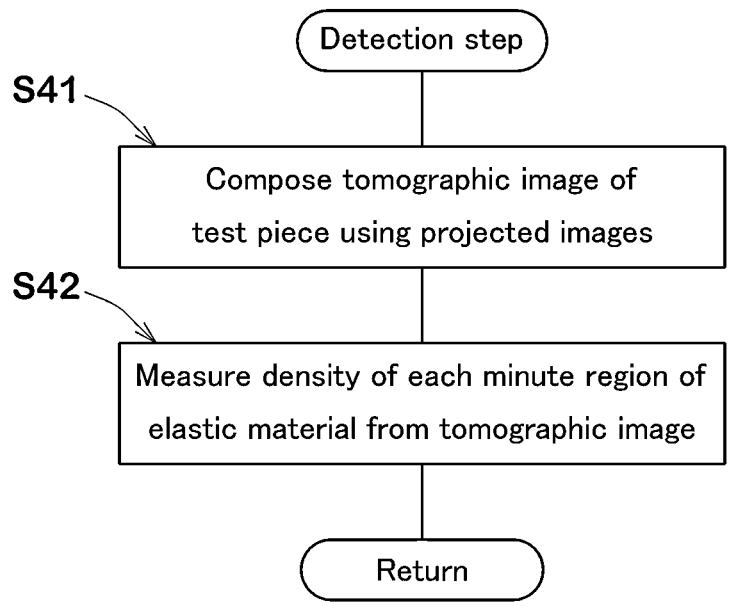
FIG. 5 is a flowchart showing the processing procedures of a detection step in accordance with the present embodiment.

In the detection step S4 according to the present embodiment, as shown in FIG. 2, the projection images of the test piece 10 (FIG. not shown) input to the projection image input unit 16A and the detection program 17A are read into the working memory 13C. Then, the detection program 17A is executed by the central processing unit 13A. Thus, the computer 8 can function as the detection unit 4 for detecting the low-density regions 15 (shown in FIGS. 4A and 4B) based on the projected images. FIG. 5 illustrates a flowchart showing the processing procedures of the detection step S4 according to the present embodiment.

[Composing Tomographic Image]

In the detection step S4 according to the present embodiment, a tomographic image 33 (shown in FIG. 4A) of the test piece 10 is composed using the projected images (step S41). In step S41 of the present embodiment, using the projected images of the test piece 10, a plurality of tomographic images 33 of the test piece 10 are obtained on an arbitrary plane that intersects perpendicularly to the axial direction of the test piece 10. FIG. 4A shows an example of them. In the present embodiment, the tomographic images 33 are obtained at an arbitrary interval (for example, 10 to 30 μm) between one end (not illustrated) and the other end 10b in the axial direction of the test piece 10 shown in FIG. 1. The number of tomographic images 33 composed in the present embodiment is 150 to 300.

[Measurement of Density]

Next, in the detection step S4 according to the present embodiment, density of each minute region of the elastic material is measured from the tomographic images 33 (shown in FIG. 4A as an example) (step S42). In step S42 of the present embodiment, in the region of the test piece 10 displayed in each tomographic image 33, the brightness value is acquired for each minute region (e.g., each pixel) that constitutes each tomographic image 33. In the present embodiment, the brightness value is the lowest in the voids 15a. Further, the higher the brightness value, the higher the density of the elastic material. Thus, a proportional relationship is established between the brightness value and the density.

Next, in step S42 of the present embodiment, the brightness value of the elastic material before receiving strain (i.e., the portion without the low-density region 15) is set to 1.0, and the brightness value in which the elastic material does not exist (the lowest brightness value) is set to 0. Then, the ratio of the brightness values of each minute region (each pixel in this example) is calculated. Each ratio of such a brightness value is defined as the normalized density (i.e., the ratio to the density of the elastic material before receiving strain).

As mentioned above, the density of the low-density regions 15 are defined as a value in a range of from 0.0 to less than 0.8 times of the density of the elastic material before the strain is applied. Thus, in step S42, the regions that are displayed by the minute regions (pixels) having the ratio of brightness values (normalized density) of 0.0 to 0.8 are detected as the low-density regions 15.

In the present embodiment, the regions that are displayed by the minute regions (pixels) having the ratio of brightness values (normalized density) less than 0.1 are defined as voids 15a. In addition, the regions that displayed by the minute regions (pixels) having the ratio of brightness values (normalized density) of 0.1 to 0.8 are detected as the low-density rubber portions 15b.

In step S42 of the present embodiment, the low-density regions 15 are detected in each tomographic image 33. To detect the low-density regions 15, commercially available image processing software (e.g., Photoshop (registered trademark) manufactured by Adobe) or the like can be used. The detection result of the low-density regions 15 is input to the detection result input unit 16B.

[Relationship Obtaining Step]

Next, in the performance evaluation method according to the present embodiment, a relationship obtaining step (S5) is conducted. The step S5 can obtain a density distribution that is a relationship between the densities of the low-density regions 15 and the frequency thereof, based on the detection result (as shown in FIG. 4A as an example) of the low-density regions 15.

In the density distribution obtaining step (S5) according to the present embodiment, as illustrated in FIG. 2, the detection result of the low-density regions 15 input to the detection result input unit 16B and the relationship obtaining program 17B are read into the working memory 13C. Then, the relationship obtaining program 17B is executed by the central processing unit 13A. This allows the computer 8 to function as the relationship obtaining unit 5 for determining the relationship between the densities in the low-density regions and the frequency thereof.

In the relationship obtaining step S5 of the present embodiment, as to the low-density regions 15 displayed in all tomographic images 33 (as an example, shown in FIG. 4A), the number of minute regions (pixels in this example) is totaled for each standardized density (ratio of brightness values). Next, in the relationship obtaining step S5, the number of minute regions having a density of 1.0 is set to "1.0", and the ratio of the number of minute regions having other densities is obtained. The ratio of such numbers is defined as a standardized frequency.

Next, in the relationship obtaining step S5 according to the present embodiment, the normalized frequency is plotted for each normalized density, with the normalized density (ratio of brightness values) on the horizontal axis and the normalized frequency (ratio of numbers) on the vertical axis. As a result, in the relationship obtaining step S5, the relationship between the densities in the low-density regions and the frequency thereof can be obtained.

Figure 6A:
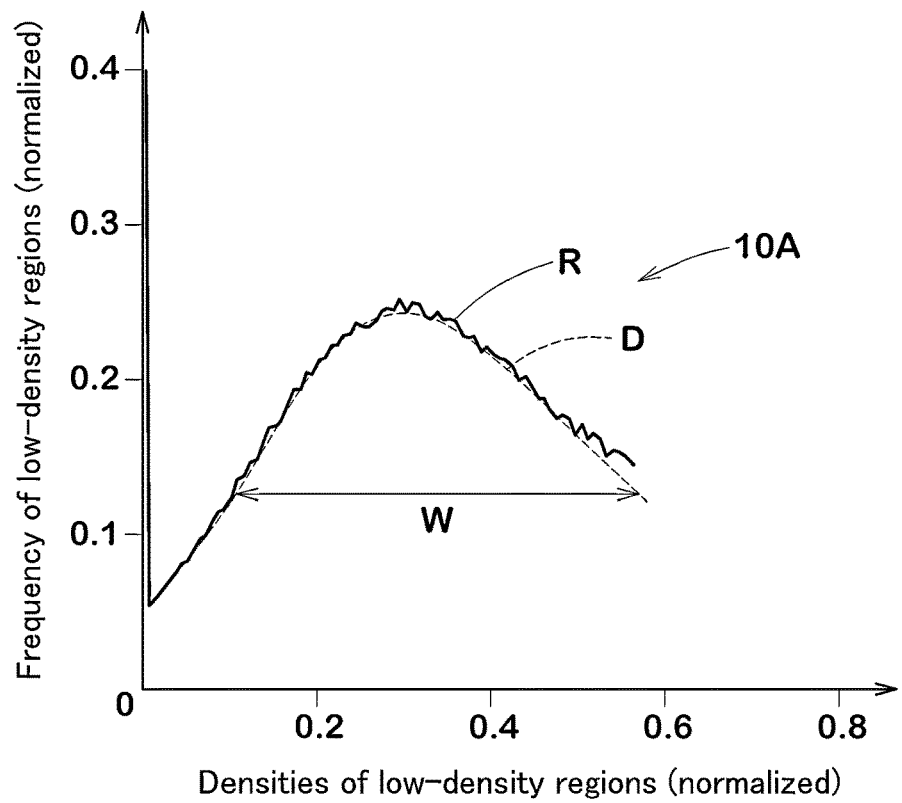
FIGS. 6A and 6B are graphs showing the relationship between the densities and frequency of the low-density regions for two types of test pieces made of elastic materials with different compositions.
Figure 6B:
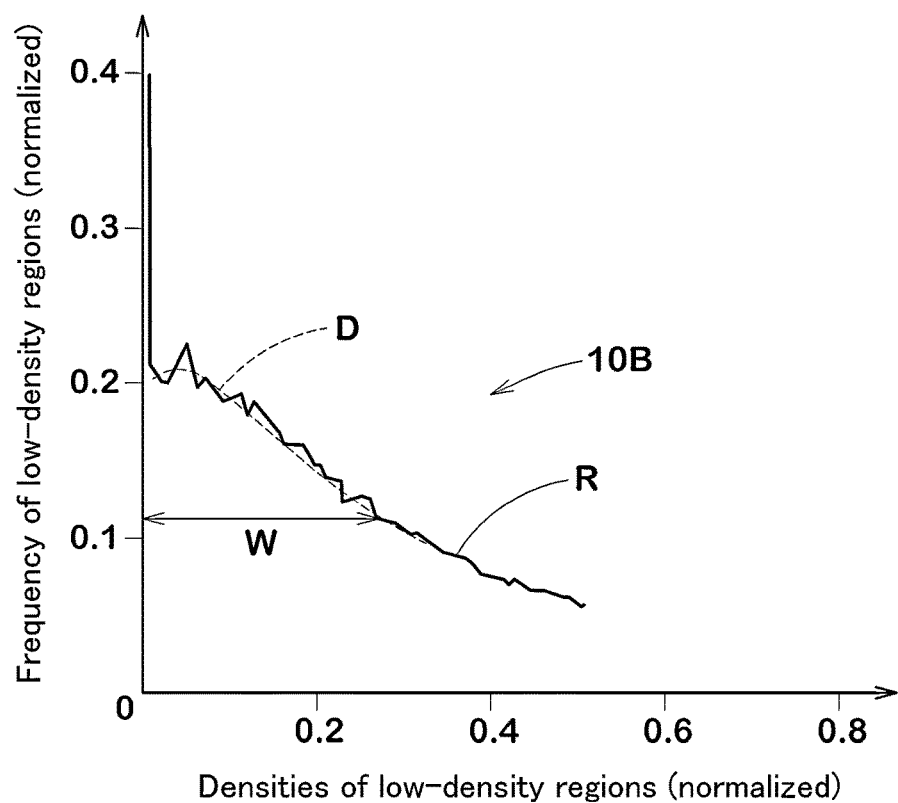

FIGS. 6A and 6B are graphs each showing the relationship (the density distribution) R between the densities in the low-density regions and frequency thereof for two types of the test pieces 10 A and 10 B made of elastic materials with different compositions. These relationships R are input to the relation input unit 16C.

[Distribution Width Calculation Step]

Next, in the performance evaluation method according to the present embodiment, the relationship R between the densities in the low-density regions and frequency thereof is approximated to normal distribution, and then a distribution width W specified by the full width at half maximum FWHM is calculated from the normal distribution (distribution width calculation step S6).

In the distribution width calculation step S6 according to the present embodiment, as illustrated in FIG. 2, the relationship R between the densities of the low-density regions and frequency thereof input to the relation input unit 16C and the distribution width calculation program 17C are read into the working memory 13C. Then, the distribution width calculation program 17C can be executed by the central processing unit 13A to make the computer 8 function as the distribution width calculation unit 6 for calculating the distribution width W.

In the distribution width calculation step S6 according to the present embodiment, the relationship R between the densities of the low-density regions 15 and frequency thereof shown in FIGS. 6A and 6B are approximated to normal distributions D. For the approximation of the normal distribution D, for example, a commercially available numerical analysis software (e.g., "MATLAB" manufactured by The MathWorks) may be used.

Next, in the distribution width calculation step S6 according to the present embodiment, the distribution width W specified by the full width at half maximum FWHM is calculated based on the normal distribution D of each relationship R. As shown in FIG. 6B, when the graph of the normal distribution D of the relationship R is interrupted at a density of 0, the distribution width W (half width at half maximum FWHM) is obtained from the graph of the normal distribution from the density 0. For example, the above numerical analysis software is used to specify the distribution width W (full width at half maximum FWHM).

The full width at half maximum FWHM is an index showing the spread of the density distribution in the low-density regions 15. Thus, the larger the full width at half maximum FWHM, the wider the densities of the low-density regions 15 are distributed. On the other hand, the smaller the full width at half maximum FWHM, the more the densities of the low-density regions 15 are locally concentrated.

According to the experiments of the inventors, it was found that there is a certain correlation between the distribution width W specified by the full width at half maximum FWHM and performance of the elastic material (e.g., wear resistance performance in this example). That is, in the elastic material having a large distribution width W, the densities of the low-density regions 15 are widely distributed. Thus, the proportion of voids 15a (shown in FIG. 4A) having a density of less than 0.1 is small, and the performance of the elastic material can be evaluated as good.

The distribution width W of the elastic material of the test piece 10A in FIG. 6A is larger than the distribution width W of the elastic material of the test piece 10B in FIG. 6B, and the frequency of the densities of less than 0.1 is small. Thus, the elastic material of the test piece 10A can be evaluated as having higher performance (wear resistance in this example) than the elastic material of the test piece 10B.

On the other hand, in the method of Patent Document 1 above, the performance (wear resistance) of the elastic material is evaluated based on the density distribution of the low-density regions 15 (total volume of the low-density region 15). However, in such a method, the density distribution (total volume) of the elastic material of the test piece 10A and the elastic material of the test piece 10B may be substantially the same, and the difference in performance cannot be evaluated.

As described above, the performance evaluation method according to the present embodiment can evaluate performance of the elastic material based on the distribution width W of the low-density regions 15. Thus, the present disclosure can improve the evaluation accuracy. The distribution width W is input to the distribution width input unit 16D (shown in FIG. 1).

[Evaluation Step]

Next, in the performance evaluation method according to the present embodiment, performance of the elastic material is evaluated based on the distribution width W (evaluation step S7).

In the evaluation step S7 according to the present embodiment, as shown in FIG. 2, the distribution width W input to the distribution width input unit 16D and the evaluation program 17D are read into the working memory 13C. Then, the evaluation program 17D can be executed by the central processing unit 13A to make the computer 8 function as the evaluation unit 7 for evaluating the performance of the elastic material.

Figure 7:
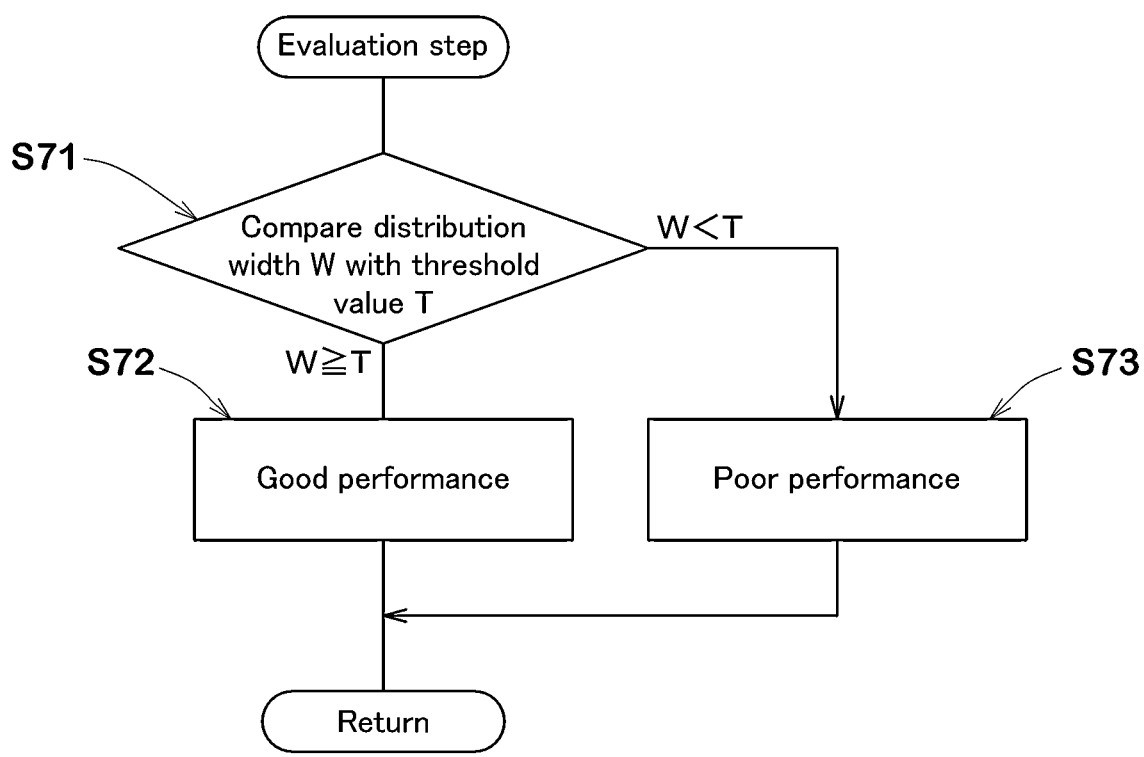
FIG. 7 is a flowchart showing the processing procedures of an evaluation step in accordance with the present embodiment.

FIG. 7 illustrates a flowchart showing the processing procedures of the evaluation step S7 according to the present embodiment. In the evaluation step S7 according to the present embodiment, the distribution width W (shown in FIG. 6A) and a predetermined the threshold value T are compared (step S71). The threshold value T can be appropriately set according to various performances (wear resistance performance in this embodiment) required for the elastic material, for example. In this embodiment, in the relationship R shown in FIG. 6A, the densities of the low-density regions 15 are defined as the ratio to the density of the elastic material before receiving the strain (e.g., from 0.0 to 0.8 in this example). In this case, the threshold is preferably set to 0.2.

In the step S71, when the distribution width W is equal to or greater than the threshold value T (0.2 in this example), the performance of the elastic material is evaluated to be good (step S72). On the other hand, in step S71, when the distribution width W is less than the threshold value T, the performance of the elastic material is evaluated to be poor (step S73). In this case, a new elastic material with a different composition is produced, and the performance evaluation method of this embodiment is carried out again. This makes it possible to reliably produce elastic materials with excellent performance.

In the present embodiment, as the performance of the elastic material, wear resistance is evaluated, but the present disclosure is not limited to such an embodiment. For example, tear resistance and/or crack resistance of the elastic material may be evaluated based on the distribution width W.

While the particularly preferable embodiments in accordance with the present disclosure have been described in detail, the present disclosure is not limited to the illustrated embodiments, but can be modified and carried out in various aspects within the scope of the disclosure.

Working Example

For elastic materials A to C, each distribution width W (full width at half maximum FWHM) was determined according to the method of the present disclosure, and the wear resistance performance was evaluated based on the results. In addition, the correlation between the results and the value of wear resistance performance in the actual vehicle running test was verified (Example). For comparison, the wear resistance performance of the elastic materials A to C was evaluated using a Ramborn tester, and then, the correlation between the results and the evaluation of wear resistance performance by the actual vehicle running test was verified (comparative example).

The reagents used are as follows.
1. Polymer (1): (one modified group)
2. Polymer (2): (two modified groups; different amount of monomer in polymer (1))
3. Polymer (3): (three modified groups: different amount of monomer in polymer (1))
4. SBR: SPRINTAN SLR6430 made by STYRON
5. BR: BR150B manufactured by Ube Industries, Ltd.
6. Denaturant: 3-(N, N-dimethylaminopropyl) trimethoxysilane manufactured by Azumax Co., Ltd.
7. Anti-aging agent: Nocrack 6C (N-1,3-dimethylbutyl-N'-phenyl-p-phenylenediamine) manufactured by Ouchi Shinko Kagaku Kogyo Co., Ltd.
8. Stearic acid: Stearin manufactured by NOF CORPORATION
9. Zinc oxide: Ginrei R manufactured by Toho Zinc Co., Ltd.
10. Aromatic oil: Diana Process AH-24 manufactured by Idemitsu Kosan Co., Ltd.
11. Wax: Sunknock wax manufactured by Ouchi Shinko Kagaku Kogyo Co., Ltd.
12. Sulfur: Powdered sulfur manufactured by Tsurumi Chemical Co., Ltd.
13. Vulcanization accelerator (1): Noxeller CZ manufactured by Ouchi Shinko Kagaku Kogyo Co., Ltd.
14. Vulcanization accelerator (2): Noxeller D manufactured by Ouchi Shinko Kagaku Kogyo Co., Ltd.
15. Silica: Ultra Jill VN3 made by Degussa
16. Silane Coupling Agent: Si69 from Degussa
17. Carbon Black: Dia Black LH (N326, N2SA: 84 m2/g) manufactured by Mitsubishi Chemical Corporation The monomers and polymers (1) to (3) were synthesized by the same procedures as that described in "Examples" of Patent Document 1. The test methods are as follows.

Distribution Width (Full Width at Half Maximum FWHM):

For elastic materials A to C, columnar test pieces with a diameter of 20 mm and an axial length of 1 mm were prepared. Then, performance of the elastic materials was evaluated according to the procedures shown in FIG. 3. In the strain applying step S2, a stress of 0.5 MPa was applied to the test pieces to generate plurality of low-density regions (voids and low-density rubber portions) inside the test pieces. Next, in the relationship obtaining step S5, the relationship between the densities of the low-density regions and the frequency of the low-density regions were obtained based on the detection results of the low-density regions. Next, in the distribution width calculation step S6, the distribution width W specified by the full width at half maximum FWHM when the relationship obtained in the relationship obtaining step S5 was approximated to the normal distribution was calculated. The larger the distribution width W, the better the wear resistance.

Ramborn Test:

For elastic materials A to C, the amount of wear was measured using a Ramborn type wear tester under the conditions of room temperature, load 1.0 kgf, and slip ratio 30%, and the reciprocal thereof were calculated. The results are shown in Table 1 using an index with elastic material A as 100, and the larger the value, the better the wear resistance performance.

Actual Vehicle Running Test:

Pneumatic tires of size 195/65R15 with treads made of elastic materials A to C were prepared. Each tire was mounted on a Japanese FF vehicle, and a groove depth of the tread at a mileage of 8000 km was measured. Then, the mileage per 1 mm of wear on the tread was calculated. The test results are shown in Table 1 using an index with the elastic material A as 100, and the larger the value, the better the wear resistance.

Table 1 shows the test results.

TABLE 1

| | Elastic materials | A | B | C |
|---|---|---|---|---|
| Composition (mass) | BR | 20 | 20 | 20 |
| | Polymer (1) | 47 | — | — |
| | Polymer (2) | — | 47 | — |
| | Polymer (3) | — | — | 47 |
| | SBR | 33 | 33 | 33 |
| | Silica | 75 | 75 | 75 |
| | Silane Coupling Agent | 6 | 6 | 6 |
| | Carbon Black | 6 | 6 | 6 |
| | Aromatic oil | 23 | 23 | 23 |
| | Stearic acid | 2 | 2 | 2 |
| | Zinc oxide | 3 | 3 | 3 |
| | Anti-aging agent | 1 | 1 | 1 |
| | Wax | 1 | 1 | 1 |
| | Sulfur | 1.5 | 1.5 | 1.5 |
| | Vulcanization accelerator (1) | 1 | 1 | 1 |
| | Vulcanization accelerator (2) | 1 | 1 | 1 |
| Example | Distribution width (half width at full width (FWHM) | 0.08 | 0.31 | 0.39 |
| Comparative example | Ramborn wear test (index) | 100 | 103 | 103 |
| | Actual vehicle driving test (index) | 100 | 113 | 119 |

As a result of the test, as shown in Table 1, it was confirmed that the method of the example had a better correlation with the actual vehicle running test than the comparative example, and that various performances of the elastic material could be evaluated with high accuracy. Furthermore, in the examples, the elastic materials B and C having a distribution width W equal to or greater than the threshold value T (0.2) are significantly superior to the elastic materials A having a distribution width W of less than the threshold value T in the actual vehicle running test. As described above, it was confirmed that the present disclosure can evaluate various performances of elastic materials with high accuracy.

The following clauses are disclosed regarding the above-described embodiments.

[Clause 1]
A performance evaluation method for elastic material including rubber or elastomer, the method comprising:
 a strain applying step of applying a strain to a test piece made of an elastic material;
 an imaging step of obtaining projected images of the test piece being strained by irradiating X-rays to the test piece;
 a detection step of detecting low-density regions in the test piece based on the projected images, wherein each low-density region is a region where density of a part of the elastic material becomes lower than that before receiving the strain;
 a relationship obtaining step of obtaining a density distribution between the densities and frequency of the low-density regions based on the detected low-density regions; and
 a distribution width calculation step of calculating a distribution width specified by a full width at half maximum FWHM from the density distribution approximated to a normal distribution.

[Clause 2]
The performance evaluation method according to clause 1, further comprising
 an evaluation step of evaluating performance of the elastic material based on the distribution width.

[Clause 3]
The performance evaluation method according to clause 2, wherein
 the evaluation step comprises
 a step of comparing the distribution width with a predetermined threshold value, and
 a step of evaluating that the performance of the elastic material is good when the distribution width is equal to or more than the threshold value.

[Clause 4]
The performance evaluation method according to clause 3, wherein
 in the density distribution, the densities of the low-density regions are defined as ratios to a density of the elastic material before receiving the strain, and
 the threshold value is 0.2.

[Clause 5]
The performance evaluation method according to any one of clauses 1 to 4, wherein
 the performance of the elastic material is wear resistance.

[Clause 6]
The performance evaluation method according to any one of clauses 1 to 5, wherein
 the detection step comprises
 a step of constructing one or more tomographic images of the test piece using the projected images, and
 a step of measuring the density of the elastic material from the one or more tomographic images.

[Clause 7]
The performance evaluation method according to any one of clauses 1 to 6, wherein the strain is a tensile strain.

[Clause 8]
The performance evaluation method according to clause 7, wherein
 the tensile strain is equal to or more than 20%.

[Clause 9]
The performance evaluation method according to any one of clauses 1 to 8, wherein
 the elastic material is rubber obtained using one or more kinds of conjugated diene compounds.

[Clause 10]
The performance evaluation method according to clause 9, wherein
 the rubber is a rubber for tires.

[Clause 11]
The performance evaluation method according to any one of clauses 1 to 10, wherein
 the X-rays have brightness equal to or more than $10^{10}$ (photons/s/mrad$^2$/mm$^2$/0.1% bw).

[Clause 12]
The performance evaluation method according to clause 11, wherein
 the brightness is equal to or more than $10^{12}$ (photons/s/mrad$^2$/mm$^2$/0.1% bw).

[Clause 13]
A performance evaluation system for elastic material including rubber or elastomer, the system comprising:
 a strain applying device for applying strain to a test piece made of an elastic material;
 an imaging device for obtaining projected images of the test piece being strained by irradiating X-rays to the test piece;
 a detection unit for detecting low-density regions in the test piece based on the projected images, wherein each low-density region is a region where density of the elastic material becomes lower than that before receiving the strain;

a relationship obtaining unit for obtaining a density distribution between the densities and frequency of the low-density regions based on the detected low-density regions; and a distribution width calculation unit for calculating a distribution width specified by a full width at half maximum FWHM when the density distribution is approximated to a normal distribution.

[Clause 14]

The performance evaluation system according to clause 13, further comprising an evaluation unit for evaluating performance of the elastic material based on the distribution width.

[Clause 15]

The performance evaluation system according to clause 13 or 14, wherein the imaging device comprises a phosphor for converting X-rays into visible light, and a decay time of the phosphor is equal to or less than 100 ms.

The invention claimed is:

1. A performance evaluation method for elastic material including rubber or elastomer, the method comprising:

a strain applying step of applying a strain to a test piece made of an elastic material, wherein the test piece is strained in an axial direction thereof;

an imaging step of obtaining projected images of the test piece being strained by irradiating X-rays to the test piece; and a detection step, executed by a central processing unit of a computer, of detecting low-density regions in the test piece based on the projected images, wherein the central processing unit executes:

a process of composing a plurality of tomographic images of the test piece on arbitrary planes that intersect perpendicularly with the axial direction of the test piece, using the projected images of the test piece, a process of acquiring a brightness value for each predetermined minute region constituting each tomographic image, a process of calculating a ratio of the brightness values of each minute region before and after receiving the strain, and a process of detecting the low-density regions with a ratio of brightness values within a predetermined value range, a relationship obtaining step of obtaining a density distribution between the densities and frequency of the low-density regions based on the detected low-density regions;

a distribution width calculation step of calculating a distribution width specified by a full width at half maximum FWHM from the density distribution approximated to a normal distribution;

selecting an elastic material as suitable for tires based on the calculated distribution width;

an evaluation step of comparing the distribution width with a predetermined threshold, evaluating that wear resistance of the elastic material is good when the distribution width is equal to or greater than the predetermined threshold, and evaluating that the wear resistance of the elastic material is poor when the distribution width is determined to be less than the predetermined threshold; and producing a tire using the elastic material evaluated to have wear resistance in the evaluation step.

2. The performance evaluation method according to claim 1, further comprising an evaluation step of evaluating performance of the elastic material based on the distribution width.

3. The performance evaluation method according to claim 2, wherein the evaluation step comprises a step of comparing the distribution width with a predetermined threshold value, and a step of evaluating that the performance of the elastic material is good when the distribution width is equal to or more than the threshold value.

4. The performance evaluation method according to claim 1, wherein the performance of the elastic material is wear resistance.

5. The performance evaluation method according to claim 1, wherein the strain is a tensile strain.

6. The performance evaluation method according to claim 5, wherein the tensile strain is equal to or more than 20%.

7. The performance evaluation method according to claim 1, wherein the elastic material is rubber obtained using one or more kinds of conjugated diene compounds.

8. The performance evaluation method according to claim 7, wherein the rubber is a rubber for tires.

9. The performance evaluation method according to claim 1, wherein the X-rays have brightness equal to or more than $10^{10}$ (photons/s/mrad$^2$/mm$^2$/0.1% bw).

10. The performance evaluation method according to claim 9, wherein the brightness is equal to or more than $10^{12}$ (photons/s/mrad$^2$/mm$^2$/0.1% bw).

11. The performance evaluation method according to claim 1, further comprising selecting an elastomer as suitable for tires based on the calculated distribution width.

* * * * *